(12) United States Patent
Breuer

(10) Patent No.: US 7,117,718 B2
(45) Date of Patent: Oct. 10, 2006

(54) DEVICE FOR ASCERTAINING A PARTICLE CONCENTRATION IN AN EXHAUST GAS FLOW

(75) Inventor: Norbert Breuer, Ditzingen (DE)

(73) Assignee: Robert Bosch GmbH, Stuttgart (DE)

( * ) Notice: Subject to any disclaimer, the term of this patent is extended or adjusted under 35 U.S.C. 154(b) by 191 days.

(21) Appl. No.: 10/218,134

(22) Filed: Aug. 12, 2002

(65) Prior Publication Data

US 2003/0046978 A1    Mar. 13, 2003

(30) Foreign Application Priority Data

Aug. 11, 2001    (DE) ................................ 101 39 615

(51) Int. Cl.
*G01N 7/02*    (2006.01)
(52) U.S. Cl. .................... 73/23.31; 73/28.01
(58) Field of Classification Search ............. 73/23–33, 73/28.01, 28.05, 28.04; 422/80
See application file for complete search history.

(56) References Cited

U.S. PATENT DOCUMENTS

| | | | | |
|---|---|---|---|---|
| 3,974,040 A | * | 8/1976 | Siebke et al. ............... 205/781 |
| 4,001,103 A | * | 1/1977 | Blurton et al. .............. 324/425 |
| 4,247,321 A | * | 1/1981 | Persinger ........................ 71/59 |
| 4,670,233 A | * | 6/1987 | Erdmannsdoerfer et al. ..... 423/213.2 |
| 4,770,760 A | * | 9/1988 | Noda et al. .................. 204/425 |
| 4,938,838 A | * | 7/1990 | Dalin et al. .................... 216/86 |
| 5,314,851 A | * | 5/1994 | Huba .......................... 502/22 |
| 5,336,081 A | * | 8/1994 | Saito et al. .................... 431/4 |
| 5,389,340 A | * | 2/1995 | Satake ....................... 73/31.05 |
| 5,486,336 A | * | 1/1996 | Dalla Betta et al. .......... 422/90 |
| 5,570,576 A | * | 11/1996 | Ament et al. .................. 60/300 |
| 5,624,640 A | * | 4/1997 | Potthast et al. ............... 422/90 |

FOREIGN PATENT DOCUMENTS

| | | |
|---|---|---|
| DE | 39 35 149 | 5/1991 |
| EP | 0 779 510 | 6/1997 |
| EP | 1006352 A2 * | 6/2000 |
| EP | 1 106 895 | 6/2001 |
| GB | 1 025 942 | 4/1966 |
| JP | 06200738 A * | 7/1994 |
| JP | 10177863 A * | 6/1998 |

* cited by examiner

*Primary Examiner*—Hezron Williams
*Assistant Examiner*—John Fitzgerald
(74) *Attorney, Agent, or Firm*—Kenyon & Kenyon LLP

(57) ABSTRACT

A device for ascertaining a particle concentration in an exhaust gas flow of a combustion device, particularly a diesel combustion device, is provided, which device ascertains very small particle concentrations in the exhaust gas of combustion devices, accompanied by high time resolution. At least one measuring unit is provided for measuring a concentration of an oxidizing agent in the exhaust gas flow, having at least one measuring element sensitive to the oxidizing agent.

26 Claims, 2 Drawing Sheets

DEVICE FOR ASCERTAINING A PARTICLE CONCENTRATION IN AN EXHAUST GAS FLOW

FIELD OF THE INVENTION

The present invention relates to a device for ascertaining a particle concentration in an exhaust gas flow.

BACKGROUND INFORMATION

Falling regulatory limit values for emissions of combustion engines, particularly of diesel engines, necessitate active emissions-reduction methods as well as methods for measuring low particle concentrations in the exhaust gas flow.

Particles from diesel engines may include a significant portion of soot and hydrocarbons absorbed on it. By optimizing the combustion processes, it has been possible to reduce the emitted particle mass. In particular, the number of large particles having diameters of more than one micrometer, which formerly contributed to the dark coloration of diesel emissions, has been drastically reduced.

Because of the low mass concentration and the small average diameter of the particles, the demands on measuring methods for determining the particle mass limited by law is increasing. This may be true in particular for particle sensors used in motor vehicles for regulating emissions-reduction components and/or the engine. In addition to sufficient accuracy and response time, suitable sensors may also be subject to requirements with respect to mechanical and thermal stresses, and at the same time, to requirements that they be manufactured in large quantities at low cost.

Sensors are already available for stationary engine test benches which, for example, may be based on the measurement of the blackening number, the opaqueness, or the gravimetric measurement of the change in the weight of a filter. These and other measuring methods may only partially satisfy the requirements indicated above.

SUMMARY OF THE INVENTION

In contrast, the present invention provides a device for ascertaining a particle concentration in an exhaust gas flow of a combustion device, particularly of a diesel combustion device, which may ascertain very low particle concentrations in the exhaust gas of combustion devices, accompanied by high time resolution.

Accordingly, an exemplary device of the present invention may include at least one measuring unit for measuring a concentration of an oxidizing agent in the exhaust gas flow using at least one measuring element sensitive to oxidizing agent.

With the aid of an exemplary measuring unit according to the present invention, an indirect measuring method may be implemented for determining the particle concentration in the exhaust gas flow based on the reaction of the oxidizing agent with the particles.

The oxidizing agent may be converted by the particles in one predefined reaction region, so that the concentration of oxidizing agent may thereby decrease in the flow direction of the exhaust gas along the reaction region.

All chemical elements or compounds may be considered as oxidizing agents which oxidatively convert at least partially with the particles under the reaction conditions present or produced in the exhaust gas, such as atmospheric air, ozone, hydrogen peroxide, nitrogen dioxide, nitric acid or the like.

In a first example embodiment of the present invention, the exhaust gas flowing out from the combustion device may already include the oxidizing agent, e.g. nitrogen dioxide, to be measured.

In a second example embodiment of the present invention, at least one storage unit may be provided for storing the oxidizing agent, In this case, for example, the oxidizing agent, e.g. hydrogen peroxide or the like, may be put into and temporarily stored in the storage unit until the moment of use, for example, in the case of mobile applications.

In a third example embodiment of the invention, at least one oxidation unit may be provided for generating the oxidizing agent. With the aid of this measure, the oxidizing agent, e.g. ozone or the like, may be generated virtually directly for determining the particle concentration, and/or may optionally be stored temporarily by the storage unit according to variant two. A separate tank-up of an appropriate oxidizing agent or of an additional working material which is transformed to form the oxidizing agent may thereby be omitted.

In a fourth example embodiment of the present invention, the oxidation unit may include at least one oxidation element for transforming the exhaust gas flow and generating the oxidizing agent. This may permit the oxidizing agent, e.g. nitrogen dioxide, etc., to be generated directly in the exhaust gas flow. An oxidation catalyst or the like, which may often be already in the exhaust branch of combustion devices, may be used for this purpose. With the aid of this variant, the configuration complexity of a device according to the present invention may be reduced.

The measuring unit may include at least two measuring elements, set apart from one another, which may be sensitive to the oxidizing agent. In this case, the distance between the two measuring elements may define the predetermined reaction region.

Alternatively or in combination with this, at least one feeding element may be provided, set apart from the measuring element, for feeding the oxidizing agent from the storage unit and/or oxidation unit to the exhaust gas flow. If desired, the distance between the feeding element and the possibly single measuring element may define the reaction region.

If the feeding element is used together with two mutually set-apart measuring elements, then the distance between the measuring elements may define the reaction region.

In principle, when using an oxidizing agent having a concentration which is known prior to being fed into the exhaust gas flow, the distance between the feeding element and the single measuring element may define the reaction region. This case may be implemented given storage of an oxidizing agent or generation of the oxidizing agent outside of the exhaust gas flow.

In general, for definition of the predetermined reaction region, alternatively the reaction region may be realized by two sampling elements, set apart from each other, or one sampling element set apart from the feeding element, each sample of the exhaust gas flow being fed to one measuring element. In this case, for example, one sample may be taken by the first sampling element in the flow direction of the exhaust gas and fed to a measuring element. If desired, using a second sampling element disposed downstream of it in the flow direction of the exhaust gas, a sample of the exhaust gas may be subsequently taken and fed, for example, to the same measuring element. In this example embodiment of the present invention, in particular the sample volumes may be comparatively small, so that a high time resolution of the example device according to the present invention may be realized.

In one further example embodiment of the present invention, at least one metering device, e.g. a controllable valve or the like, may be provided for the metered feeding of the oxidizing agent to the exhaust gas flow. With this measure, a predefined quantity of the oxidizing agent may be fed to the exhaust gas flow. In this context, the quantity to be metered may be a function of the reactivity of the oxidizing agent and/or of the particle concentration to be expected.

Greatly differing metering strategies with changing metering quantities and/or metering times, particularly an alternating switching on and off of the oxidizing agent flow, may optionally be stored in the control or evaluation unit and implemented by it. Improved measurement resolution and a higher measuring range dynamic of the device according to the present invention may be realized in this manner.

In one example embodiment of the invention, the metering quantity of the oxidizing agent may be changed as a function of the residual concentration of oxidizing agent ascertained at the measuring element. For example, a so-called automatic measuring-range switchover may thereby be implemented. Optionally, the oxidizing agent may be apportioned to the exhaust gas flow in different measuring steps, for example, first with approximately 20 ppm, then with approximately 50 ppm, subsequently with approximately 100 ppm, after that with approximately 500 ppm, then with approximately 1000 ppm, etc. In so doing, the different measuring steps may be changed until a desired measuring of the residual concentration of oxidizing agent in the exhaust gas flow, and thus determination of relatively low particle concentrations in the exhaust gas flow may be ensured.

Different families of characteristics may be stored in the control or evaluation unit, which in particular may include the connection between oxidizing agent concentration and particle concentration and/or the load moment of the combustion device with the particle quantity or concentration to be expected. For example, the above-mentioned measuring steps may be preselected on the basis of the connection between the load moment of the combustion device ascertained by an appropriate sensor, with the particle quantity to be expected. In particular, a desirable time resolution of the present invention may be realized in this manner.

The metered quantity of the oxidizing agent may be adjustable as a function of the reaction conditions prevailing in the reaction region, particularly the temperature. The temperature in the reaction region may be ascertained by a temperature sensor, and in particular, the signal may be forwarded to the control or evaluation unit. This may make it possible to allow for the decrease in the oxidizing agent concentration or quantity, detected at the measuring element, by an altered, particularly higher reaction temperature, and optionally to distinguish from an increase or change of the particle concentration in the exhaust gas flow. Therefore, using this example embodiment of the present invention, a compensation of temperature influences on the measurement may be implemented, which may be used for a comparatively precise determination of the particle concentration in the exhaust gas flow.

The particle concentration in the exhaust gas flow may be ascertained by forming the difference between the metered-in or measured oxidizing agent quantity or concentration of the oxidizing agent at the location of the first measuring element or feeding element, and the remaining oxidizing agent quantity or concentration of the oxidizing agent at the location of the second measuring element or at the end of the reaction region. The particle quantity present in the exhaust gas may correlate with this differential value.

By altering the quantity of oxidizing agent used, primarily cross-sensitivities with respect to other oxidizing agents such as, for example, oxygen or other substances contained in the exhaust gas, which are not to be verified, may be reduced or eliminated. In this case, in particular a precise metering of the oxidizing agent quantity or determination of the oxidizing agent concentration at the front end of the reaction region in the direction of flow of the exhaust gas may be required to be provided.

The signal of the measuring element at the rear end of the reaction region in the direction of flow of the exhaust gas may be used for controlling or regulating the quantity of oxidizing agent to be metered, that is to say, may be used primarily for switching over the measuring range or altering the measuring step.

In one example embodiment of the present invention, at least one flow divider unit may be provided for dividing the exhaust gas flow into at least two partial flows. Therefore only one of the partial flows may be used for determining the particle concentration in the exhaust gas flow, and primarily with the aid of the control or evaluation unit, conversion may be made to the quantity of particles in the entire exhaust gas flow. To this end, the flow divider device may include at least the measuring element(s), the feeding element, the oxidation element and/or the metering device, so that the particle concentration may be determined in the manner indicated above.

At least one cooling and/or heating unit may be provided for cooling or heating the exhaust gas flow and/or its partial flows. A thermostatting of the exhaust gas flow and/or its partial flows may thereby be implemented. Therefore, the above-mentioned cross-sensitivity may be reduced or completely eliminated with respect to the temperature of the exhaust gas flow and/or its partial flows, permitting a comparatively precise measurement of the particle quantity in the exhaust gas flow.

In one example embodiment of the present invention, at least one particle filter may be provided for filtering the particles in the exhaust gas flow. With the aid of such a particle filter, the particle concentration may be integrated or summed up over a certain time range. For this purpose, the particle filter, already frequently present, of corresponding combustion devices may be used for this example embodiment.

At least the particle filter may be disposed in the direction of flow of the exhaust gas upstream from a measuring element. In addition to the determination of the particle concentration in the exhaust gas flow, a functional check of the particle filter may be implemented at the same time due to this arrangement of the particle filter and the measuring element, respectively.

For example, if oxidizing agent is metered at time intervals of several seconds or minutes, then if the filter is intact, an integral value over the particle quantity deposited in the filter may result as the measuring signal of the measuring element. If, on the other hand, the particle filter is impaired, for example, broken or such thing, then the measuring signal of the measuring element may correspond essentially to the particle concentration predominating at the moment, which in this case may lie below the integrated signal to be expected. Therefore, the device of the present invention may additionally be constructed as an on-board monitoring device for the use of particle filters of a combustion device, particularly of a vehicle.

When using the oxygen already present in the exhaust gas flow of the combustion device as oxidizing agent, heating of the exhaust gas flow by the corresponding heating unit to above 500° C. may be provided, so that oxidation of the particles, particularly of the soot, occurs.

In the measurement of nitrogen oxides, particularly nitrogen dioxide, as oxidizing agent, heating of the exhaust gas flow by the corresponding heating unit to more than 350° C. may be provided for oxidation of the particles.

Particularly for the example embodiments of the present invention in which heating and/or cooling may be required to be provided, the flow divider device may be used, where in particular the partial flow of the exhaust gas to be examined is to be substantially smaller than the total exhaust gas flow. For example, the partial flow to be analyzed may include only approximately 1 per mille content to 10 percent of the total flow, the total particle quantity in the exhaust gas flow being ascertained by the control or evaluation unit.

A example device of the present invention may be configured in such a manner that the time resolution may be realized between a fraction of a second and several minutes. To this end, for example, the reaction region, the flow velocity of the exhaust gas in the reaction region and the sampling volume may be configured accordingly.

If desired, secondary air may be apportioned with a predefined quantity to the reaction region. In this case, the oxidizing agent may be available comparatively easily and conveniently, and moreover, may have a relatively constant, known oxygen concentration. When working with this example embodiment of the present invention, in accordance with the above-indicated examples to this effect, the exhaust gas flow or of a corresponding partial flow to be measured may be heated to approximately 500 to 600° C.

A mixture of the oxidizing agent with the exhaust gas flow may be implemented using suitable elements and/or measures. Ascertainment of the volumetric flow of the exhaust gas may be desirable for specific application cases.

DETAILED DESCRIPTION

Figure 1:
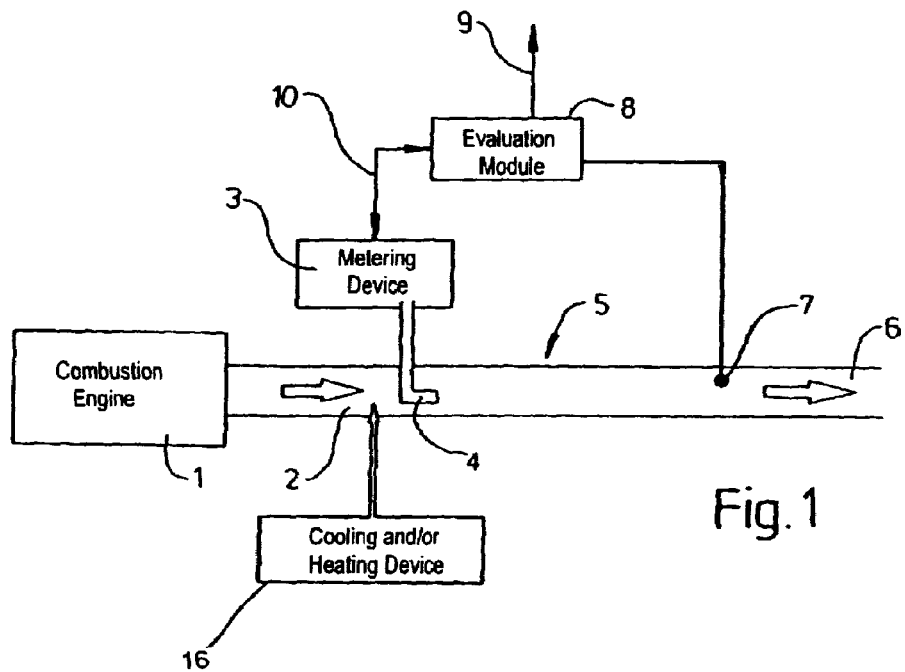
FIG. 1 shows a schematic block diagram of an example device according to the present invention.

FIG. 1 shows a block diagram of an example device according to the present invention having a combustion engine 1. Combustion engine 1 generates raw exhaust gas 2 having particles (not shown). The quantity or concentration of particles in raw exhaust gas 2 is ascertained indirectly with the aid of an oxidizing agent.

A metering device 3 stores and/or generates the oxidizing agent and apportions it to raw exhaust gas 2 via a feeding element 4. A reaction region 5 is formed between the feeding element and a sensor 7 for measuring the concentration of oxidizing agent. In reaction region 5, the soot in raw exhaust gas 2 is transformed in particular by the oxidizing agent, so that an exhaust gas 6 passes off having reduced oxidizing agent concentration.

Sensor 7 generates, in particular, a signal which is provided to an evaluation module 8. Evaluation module 8 is connected by a signal line 10 to metering device 3, so that evaluation module 8 ascertains the particle concentration by forming the difference between the quantity of oxidizing agent used and the remaining quantity of oxidizing agent in raw exhaust gas 2 and exhaust gas 6, respectively.

Evaluation module 8 may control and regulate metering device 3, and thus the quantity of oxidizing agent apportioned. The ascertained particle concentration is optionally made available via a signal line 9 to a control or monitoring unit (not shown) of a vehicle or the like.

Figure 2:
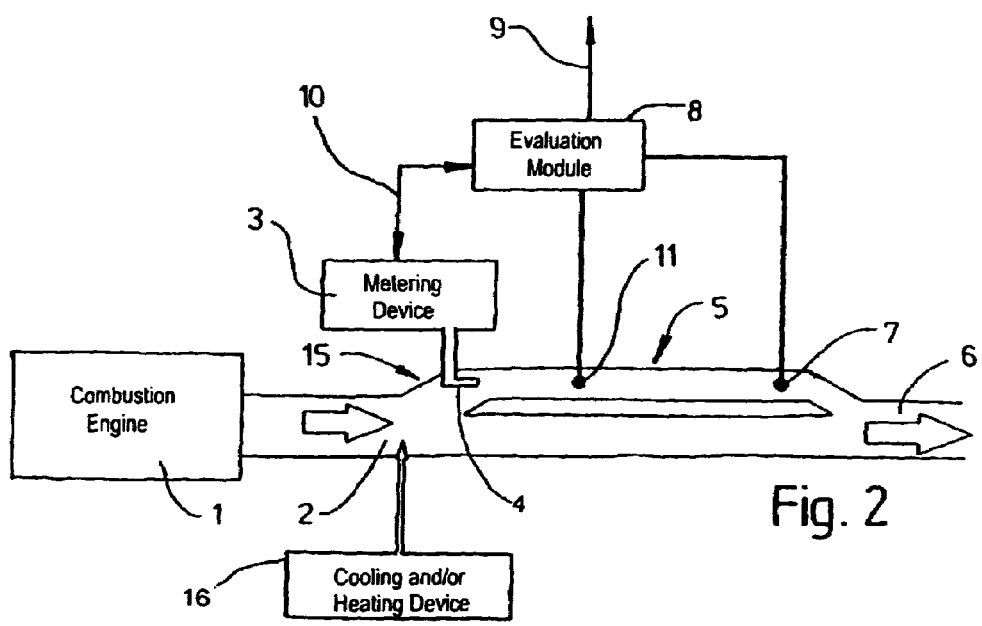
FIG. 2 shows a schematic block diagram of an example device according to the present invention having a flow divider.

FIG. 2 shows an example embodiment of the present invention, raw exhaust gas 2 being divided by a flow divider 15 into two separate partial flows. In this case, for example, the smaller partial flow, in accordance with the example shown in FIG. 1, is analyzed, i.e., its particle concentration is determined, and extrapolated to the total raw exhaust gas 2 by evaluation module 8.

In contrast to the example embodiment according to FIG. 1, the example embodiment according to FIG. 2 has a temperature sensor 11 for determining the reaction temperature of reaction region 5. Among other things, with the aid of relevant temperature sensor 11 and evaluation module 8, both the metering quantity of the oxidizing agent may be changed as a function of the reaction conditions in reaction region 5, and the temperature sensitivity of the oxidizing agent reaction may be compensated to the greatest extent possible.

Figure 3:
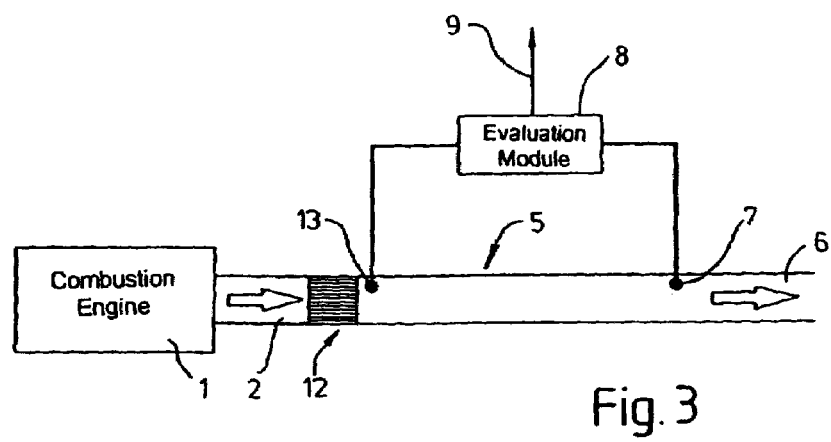
FIG. 3 shows a schematic block diagram of an example device according to the present invention having an oxidation unit.

FIG. 3 shows a further example embodiment of the present invention in which, in contrast to the example embodiments described before, an oxidation device 12, e.g. an oxidation catalyst, is provided for generating an oxidizing agent, for example, nitrogen dioxide, in raw exhaust gas 2. In this case, an exact knowledge of the oxidizing agent concentration at the front end of reaction region 5 in the direction of flow of raw exhaust gas 2 is realized using a second sensor 13. Therefore, reaction region 5 is formed between sensor 13 and sensor 7, evaluation module 8 using the difference between the two signals for determining the particle concentration in raw exhaust gas 2.

Figure 4:
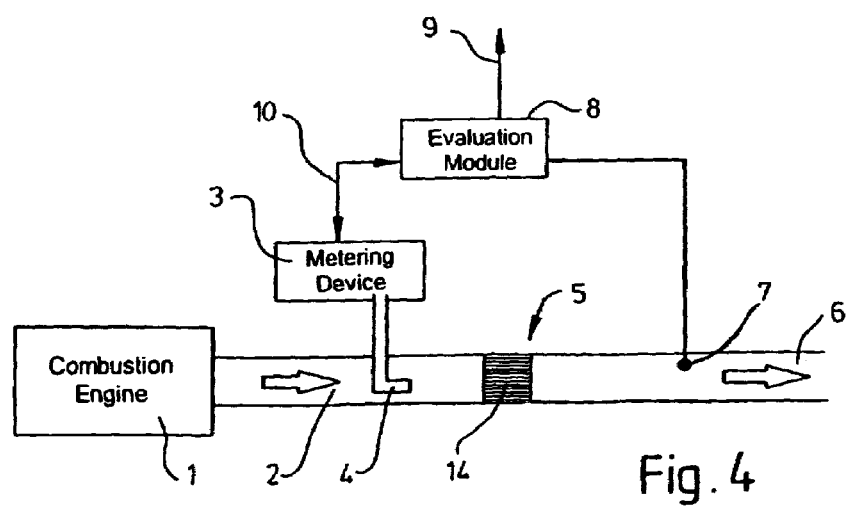
FIG. 4 shows a schematic block diagram of an example device according to the present invention having a particle filter.

FIG. 4 shows a fourth example embodiment of the present invention, in which, in particular, a particle filter 14 is disposed in reaction region 5. With the aid of this arrangement, a functional check of particle filter 14 may be implemented by the device of the present invention.

Particle filter 14 sums up or integrates the particles in the course of time, so that if particle filter 14 is intact, an integral value over the particle quantity deposited in particle filter 14 results as the measuring signal of sensor 7. However, if particle filter is damaged or broken, then the measuring signal of sensor 7 corresponds essentially to the particle concentration predominating at the moment, which lies below the expected integrated signal.

The example embodiments shown in the figures may be combined according to the invention in widely varying fashion. For example, a flow divider 15 and/or a temperature sensor 11 may also be provided for the example embodiments according to the other respective figures.

Moreover, as depicted in figures 1 and 2, a thermostatting, for example, with the aid of a cooling and/or heating device 16, may also be implemented in the example embodiments shown in the figures. An appropriate thermostatting of raw exhaust gas 2 may permit, in particular, a reduction of measuring inaccuracies which may be caused, for example, because of temperature fluctuations in raw exhaust gas 2, and thus altered reaction conditions in reaction region 5.

What is claimed is:

1. A device for ascertaining a particle concentration in an exhaust gas flow of a combustion device, comprising:
   at least one measuring unit for measuring a concentration of an oxidizing agent in the exhaust gas flow, the at least one measuring unit including at least one measuring element sensitive to the oxidizing agent;
   at least one oxidation unit for generating the oxidizing agent; and
   at least one metering device for metering a feeding of the oxidizing agent to the exhaust gas flow.

2. The device according to claim 1, wherein the at least one oxidation unit includes at least one oxidation element for transforming the exhaust gas flow and for generating the oxidizing agent.

3. A device for ascertaining a particle concentration in an exhaust gas flow of a combustion device, comprising:
   at least one measuring unit for measuring a concentration of an oxidizing agent in the exhaust gas flow, the at least one measuring unit including at least one measuring element sensitive to the oxidizing agent;
   at least one feeding element for feeding the oxidizing agent to the exhaust gas flow from at least one of a storage unit and an oxidation unit, the at least one feeding element being set apart from the at least one measuring element; and
   at least one metering device for metering a feeding of the oxidizing agent to the exhaust gas flow.

4. A device for ascertaining a particle concentration in an exhaust gas flow of a combustion device, comprising:
   at least one measuring unit for measuring a reduction in a concentration of an oxidizing agent in the exhaust gas flow, the at least one measuring unit including at least one measuring element sensitive to the oxidizing agent; and
   at least one metering device for metering a feeding of the oxidizing agent to the exhaust gas flow;
   wherein the at least one measuring unit includes at least two measuring elements set apart from each other and which are sensitive to the oxidizing agent.

5. A device for ascertaining a particle concentration in an exhaust gas flow of a combustion device, comprising:
   at least one measuring unit for measuring a reduction in a concentration of an oxidizing agent in the exhaust gas flow, the at least one measuring unit including at least one measuring element sensitive to the oxidizing agent; and
   at least one metering device for metering a feeding of the oxidizing agent to the exhaust gas flow.

6. The device according to claim 5, wherein the combustion device is a diesel engine.

7. The device according to claim 5, further comprising:
   at least one storage unit for storing the oxidizing agent.

8. The device according to claim 5, wherein the oxidizing agent includes one of air, ozone, hydrogen peroxide, nitrogen oxide or nitric acid.

9. The device according to claim 5 wherein the oxidizing agent is a substance that oxidatively converts at least partially with particles in the exhaust gas flow under reaction conditions in the exhaust gas flow.

10. The device according to claim 5, further comprising:
    at least one particle filter for filtering particles in the exhaust gas flow.

11. The device according to claim 10, wherein the at least one particle filter is disposed in a flow direction of the exhaust gas upstream from the at least one measuring element.

12. A vehicle, comprising:
    a combustion device;
    a device for ascertaining a particle concentration in an exhaust gas flow of the combustion device, the device including at least one measuring unit for measuring a concentration of an oxidizing agent in the exhaust gas flow, the at least one measuring unit including at least one measuring element sensitive to the oxidizing agent; and
    at least one metering device for metering a feeding of the oxidizing agent to the exhaust gas flow.

13. The vehicle according to claim 12, wherein the combustion device is a diesel internal combustion engine.

14. The vehicle according to claim 12, wherein the oxidizing agent includes one of air, ozone, hydrogen peroxide, nitrogen oxide or nitric acid.

15. The vehicle according to claim 12, wherein the oxidizing agent is a substance that oxidatively converts at least partially with particles in the exhaust gas flow, under reaction conditions in the exhaust gas flow.

16. A method for ascertaining a particle concentration in an exhaust gas flow of a combustion device, comprising:
    arranging at least one measuring unit for measuring the particle concentration in the exhaust gas flow; and
    arranging at least one measuring element in the at least one measuring unit, the at least one measuring element being sensitive to an oxidizing agent in the exhaust gas flow; and
    arranging at least one metering device to meter a feeding of the oxidizing agent to the exhaust gas flow.

17. The method according to claim 16, wherein the combustion device includes a diesel internal combustion engine.

18. The method according to claim 16, wherein the oxidizing agent includes one of air, ozone, hydrogen peroxide, nitrogen oxide or nitric acid.

19. The method according to claim 16, wherein the oxidizing agent is a substance that oxidatively converts at least partially with particles in the exhaust gas flow, under reaction conditions in the exhaust gas flow.

20. A vehicle, comprising:
    a combustion device;
    a device for ascertaining a particle concentration in an exhaust gas flow of the combustion device, the device including at least one measuring unit for measuring a concentration of an oxidizing agent in the exhaust gas flow, the at least one measuring unit including at least one measuring element sensitive to the oxidizing agent;
    at least one oxidization unit for generating the oxidizing agent; and
    at least one metering device for metering a feeding of the oxidizing agent to the exhaust gas flow.

21. A vehicle, comprising:
    a combustion device;
    a device for ascertaining a particle concentration in an exhaust gas flow of the combustion device, the device including at least one measuring unit for measuring a reduction in a concentration of an oxidizing agent in the exhaust gas flow, the at least one measuring unit including at least one measuring element sensitive to the oxidizing agent, the measurement being based on a determination by the at least one measuring element of at least one concentration of the oxidizing; and at least one metering device for metering a feeding of the oxidizing agent to the exhaust gas flow.

22. A method for ascertaining a particle concentration in an exhaust gas flow of a combustion device, comprising:
arranging at least one measuring unit for measuring the particle concentration in the exhaust gas flow of the combustion device;
arranging at least one measuring element in the at least one measuring unit, the at least one measuring element being sensitive to an oxidizing agent in the exhaust gas flow, the at least one measuring element configured to measure a reduction in a concentration of the oxidizing agent in the exhaust gas flow, the measurement being based on a determination by the at least one measuring element of at least one concentration of the oxidizing agent; and
arranging at least one metering device to meter a feeding of the oxidizing agent to the exhaust gas flow.

23. A vehicle, comprising:
a combustion device;
a device for ascertaining a particle concentration in an exhaust gas flow of the combustion device, the device including at least one measuring unit for measuring a reduction in a concentration of an oxidizing agent in the exhaust gas flow, the at least one measuring unit including at least one measuring element sensitive to the oxidizing agent, the measurement being based on a determination by the at least one measuring unit of at least one concentration of the oxidizing agent;
at least one oxidization unit for generating the oxidizing agent; and
at least one metering device for metering a feeding of the oxidizing agent to the exhaust gas flow.

24. A method for ascertaining a particle concentration in an exhaust gas flow of a combustion device, comprising:
arranging at least one measuring unit for measuring the particle concentration in the exhaust gas flow;
arranging at least one measuring element in the at least one measuring unit for measuring a reduction in a concentration of an oxidizing agent in the exhaust gas flow, the at least one measuring element being sensitive to an oxidizing agent in the exhaust gas flow; and
arranging at least one metering device to meter a feeding of the oxidizing agent to the exhaust gas flow.

25. A device for ascertaining a particle concentration in an exhaust gas flow, comprising:
at least one measuring unit for measuring a concentration of an oxidizing agent in the exhaust gas flow, the at least one measuring unit including at least one measuring element sensitive to the oxidizing agent; and
at least one flow divider unit for dividing the exhaust gas flow into at least two partial flows;
wherein the at least one flow divider unit includes at least one of: i) the at least one measuring element, ii) a feeding element, iii) an oxidation element, and iv) a metering device.

26. The device according to claim 25, further comprising:
at least one of a cooling unit for cooling and a heating unit for heating at least one of the exhaust gas flow and the partial flows.

* * * * *